United States Patent [19]

Pålsgård et al.

[11] Patent Number: 5,767,821

[45] Date of Patent: Jun. 16, 1998

[54] COMMUNICATION DEVICE

[76] Inventors: Göte Pålsgård, S-702 11, Örebro; Lars-Olov Östlin, S-822 00, Alfta, both of Sweden

[21] Appl. No.: 730,958

[22] Filed: Oct. 16, 1996

Related U.S. Application Data

[63] Continuation of Ser. No. 855,695, filed as PCT/SE90/00718, Nov. 6, 1990, abandoned.

[30] Foreign Application Priority Data

Nov. 7, 1989 [SE] Sweden ................................. 8903713

[51] Int. Cl.$^6$ ............................................. G09G 5/00
[52] U.S. Cl. .................................... 345/8; 345/32
[58] Field of Search ............................... 345/156, 157, 345/7, 8, 32; 250/221, 221.1; 341/22, 23, 21; 351/209, 210; 273/140 B, 18; 354/62

[56] References Cited

U.S. PATENT DOCUMENTS

| | | |
|---|---|---|
| 3,462,604 | 8/1969 | Mason . |
| 3,724,932 | 4/1973 | Cornsweet et al. ............... 351/210 |
| 3,804,496 | 4/1974 | Crane et al. . |
| 4,028,725 | 6/1977 | Lewis . |
| 4,109,145 | 8/1978 | Graf . |
| 4,145,122 | 3/1979 | Rinard et al. . |
| 4,613,219 | 9/1986 | Vogel ............................. 351/209 |
| 4,743,200 | 5/1988 | Welch et al. ..................... 345/8 |
| 4,852,988 | 8/1989 | Velez et al. ...................... 351/209 |
| 4,891,630 | 1/1990 | Friedman et al. ................ 345/156 |
| 4,946,271 | 8/1990 | Palsgard et al. ................. 351/210 |

FOREIGN PATENT DOCUMENTS

| | | |
|---|---|---|
| 0 270 636 | 5/1991 | European Pat. Off. . |
| 1-241511 | 9/1989 | Japan . |
| 1-274736 | 11/1989 | Japan . |
| 8601963 | 3/1986 | WIPO . |
| 8707497 | 12/1987 | WIPO . |

OTHER PUBLICATIONS

Behavior Research Methods & Instrumentation, Editor, Joseph B. Sidowski, University of South Florida, Tampa, FL, vol. 7, pp. 397–429, 1975.

Fixation Point Measurement by the Oculometer Technique by John Merchant Optical Engineering, vol. 13–No. 4 –Jul./Aug. 1974.

Second International Conference on Rehabilation Engineering Combined with the Resna 7th Annual Conference, Proceedings, Ottawa, Canada, 17–22 Jun./Jul. 1984, pp. 448–449.

Proceedings of the Workshop on Communication Aids for the Non–Verbal Physically Handicapped, Held at the University of Ottawa, Ottawa, Ontario, Canada, 8–10 Jun. 1977.

Globecom'85 IEEE Global Telecommunications Conference, Conference Record V. 3 of 3, pp. 1063–1065.

*Primary Examiner*—Chanh Nguyen
*Attorney, Agent, or Firm*—McAulay Fisher Nissen Goldberg & Kiel, LLP

[57] ABSTRACT

A communication device has a carrier on which a picture emitting element, an optical system, and a light sensitive element are mounted. The carrier is positionable closely in front of and in a predetermined position with respect to an eye to be examined of a person. The optical system is arranged to direct an image of the eye on the light sensitive element. An evaluating unit is provided for evaluating direction information from the light sensitive element so as to generate a signal encoding the direction of the gaze of the person. The evaluating unit selects, from the image of the eye on the light sensitive element, at least two pieces of image information emanating from the eye of the person upon said light sensitive element, the mutual distance on the light sensitive element of which is a function of the angle made by the gaze direction of the eye with the optical axis of the optical system and substantially independent of small lateral displacements between the carrier and the eye of the person. The evaluating unit includes componentry for calculating the gaze angle of the person from the pieces of image information.

10 Claims, 5 Drawing Sheets

COMMUNICATION DEVICE

This is a continuation of application Ser. No. 07/855,695, filed May 4, 1992, now abandoned which was a National Phase of PCT application Ser. No. PCT/SE90/00718 filed Nov. 6, 1990.

FIELD OF THE INVENTION AND BACKGROUND

The present invention relates to a device for making it possible for disabled persons without capability to speak and to move their arms to communicate with the environment. A device of this type is known by U.S. Pat. No. 4,946,271 and remedies the inconveniences of already known devices for communication with the environment by determination of the gaze direction of a person, as far as the necessities to show a picture with said symbols is concerned to the person in question in a fixed position with respect to one of the eyes of the person and the arrangement of the means determining the gaze direction of the person looking at said picture in a fixed position with respect to one eye of the person.

By the arrangement of the picture emitting element and the light sensitive element registering an image of the eye of the person on a carrier, which is located closely in front of the eyes of the person and in a predetermined position with respect to the eye to be examined, the drawbacks associated with the devices already known were avoided, in which it was necessary that the person would hold his eye in a determined position with respect to the picture shown as well as the means determining the gaze direction so as to make the device in question able to function.

However, although a person using this already known communication device for communicating with the environment when communicating may turn his head in an arbitrary direction and accordingly is not in any way restricted in motion or position, errors may arise in the determination of towards what on the picture shown the person is directing his gaze since the carrier is displaced somewhat laterally with respect to the eye of the person. The definition for lateral displacement comprises displacements in the vertical direction as well as in the horizontal direction. It will be sufficient for the person in question to contract his nose at one single occasion so as to generate such a displacement. Other face movements or displacements of the head of the person may also cause a certain lateral displacement of the carrier with respect to the eye of the person. Since the gaze direction of the eye of the person in this device is determined by detecting the position of the pupil on an image of the eye thrown upon the light sensitive element, a lateral displacement of this kind will, after an adjustment and testing of the device previously made, make the evaluating unit make incorrect conclusions as to what on the picture shown the person is holding his gaze at, so that a new adjustment with a testing run becomes necessary. Lateral displacements of one or some millimetres will be enough to cause such errors. Not only will it be necessary for a person having, for any reason, difficulties to hold his face parts still to irritatingly often readjust the device, but the person may also deliver messages leading to other results than he intended.

BRIEF DESCRIPTION OF THE INVENTION

The object of the present invention is to provide a device of the type defined in the introduction, but which eliminates the drawbacks as discussed above of the device already known of this type and enables a reliable determination of towards what on the picture shown said person directs his gaze independently of small lateral displacements between the carrier and the eye of the person and without necessitating any readjustment after an initial adjustment and such a relative displacement.

According to the invention this object is obtained by providing a device of the type defined in the introduction with means arranged to enable the optical system to throw at least two pieces of image information emanating from the eye of the person upon said light sensitive element, the mutual distance on the light sensitive element of which is a function of the angle made by the gaze direction of the eye with the optical axis of the optical system and independent of possible small lateral displacements between the carrier and the eye of the person, and that the evaluating unit is arranged to calculate said angle and thus the gaze direction of the person from said pieces of information.

Through the understanding according to the invention that it is possible, from an image of an eye of a person generated by light reflected from this eye, to obtain two picture information parameters, the mutual distance of which is a function of the angle which the gaze direction of the eye makes with the optical axis of the optical system and independent of small lateral displacements between the carrier and the eye of the person, a device for reliable communication with the environment, controlling machines or the like without any requirement of an exact lateral fixation of the carrier of the device may be provided. According to the invention such a device is obtained by providing it with the means discussed above and adapting the evaluating unit in the way mentioned above.

According to a preferred embodiment of the invention one of said image information parameters consists of a light reflex emanating from the cornea of the eye and the other piece of image information is an image of a point being arranged to follow the eye in its movement. An example of such a point is the pupil opening of the eye, the image information parameter used in such a case being preferably one outer border of the pupil opening. The special features of the cornea sphere of the eye regarding the reflection of light inciding thereon are utilized in this preferred embodiment.

Further preferred features and advantages of the device according to the invention will appear from the other dependent claims and the appended description.

BRIEF DESCRIPTION OF THE DRAWINGS

With reference to the appended drawings, below follows a specific description of a preferred embodiment of the invention cited as an example.

In the drawings.

DETAILED DESCRIPTION OF A PREFERRED EMBODIMENT OF THE INVENTION

It should be pointed out that the invention is not in any way restricted to devices intended to be used by disabled persons, but the invention may just as well be applied to different work situations and the like in which a sound and healthy person may find himself and in which the same has his hands occupied or for any other reason wishes to use his eye for communicating with any other person, controlling a machine or the like.

Figure 1:
FIG. 1 is a schematic perspective view of a person using the device according to the invention.

A disabled person using the communication device according to the invention is shown in FIG. 1, but as mentioned the device could also be used by for example a pilot. The device has an optical unit 1, which is arranged on a, for example spectacle-frame-like, carrier 2 arranged in a fixed distance in front of the eyes of the user, so that the optical unit is arranged directly in front of one eye of the user. Leads run from the optical unit 1 to a central processing unit 3 located at an arbitrary, suitable place, which contains means for controlling different functions of the optical unit and to which further equipment is connectable.

Figure 2:
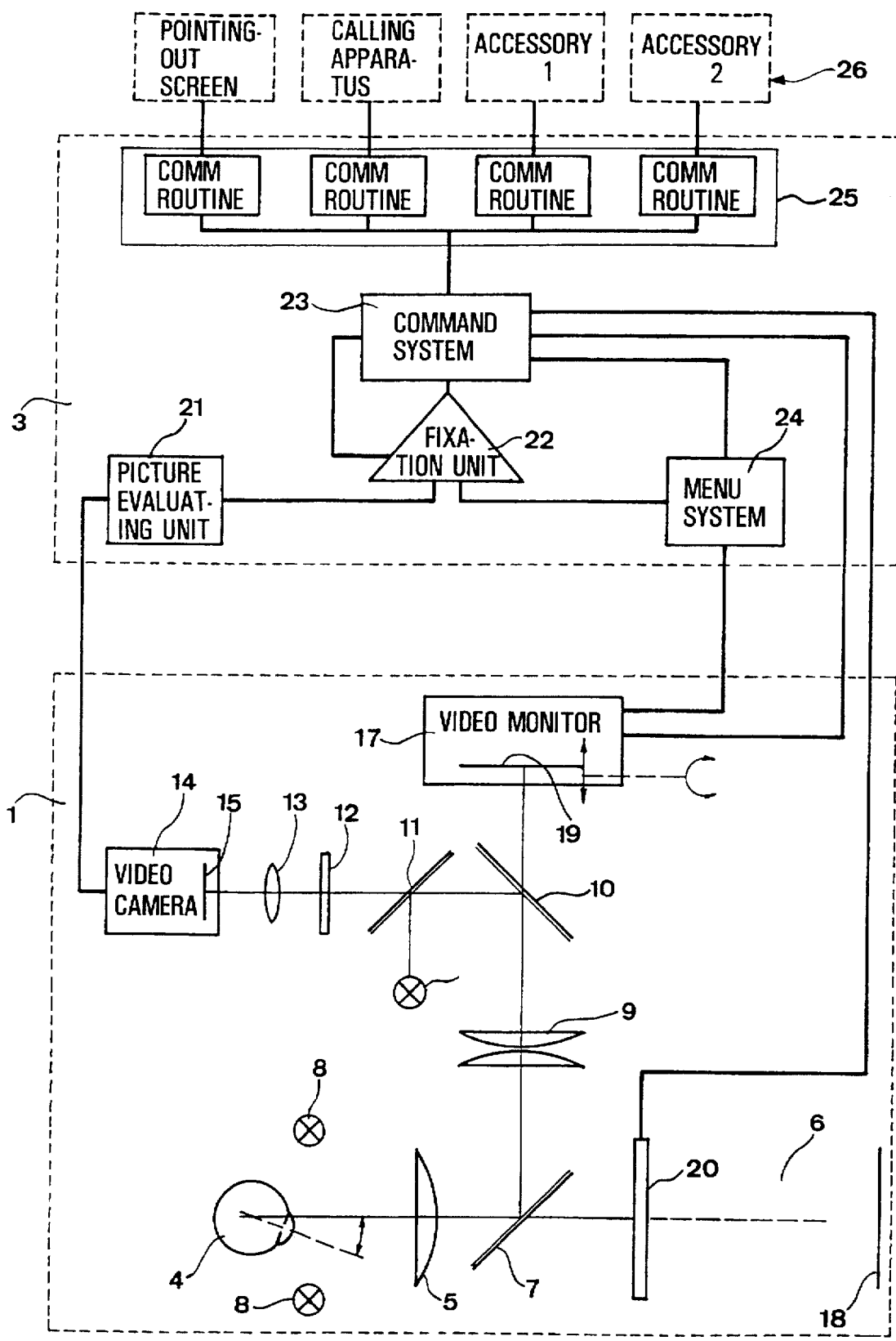
FIG. 2 is a diagram illustrating the construction and the function of a device according to a preferred embodiment of the invention.
Figure 3:
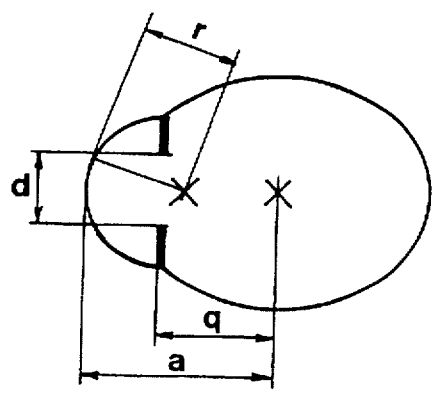
FIGS. 3–6 are views contributing to the explanation of the optical considerations on which the design of the device according to the preferred embodiment of the invention are based upon.
Figure 4:
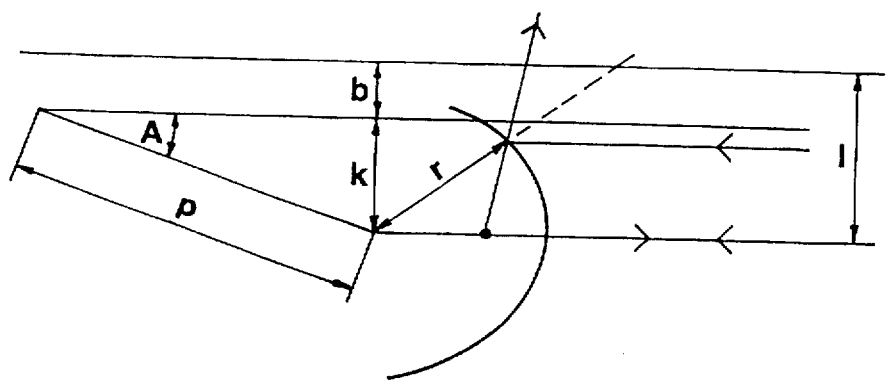

The function of the device according to the invention will now be described with reference to FIG. 2, in which the optical unit 1 arranged on the carrier and the central unit 3. Each has been framed in by dashed lines. One of the eyes of the person is provided with the reference 4. A spectacle lens 5 is arranged in front of the eye 4 of the person for correcting possible visual defects. The eye 4 looks at the environment 6 through a first plane mirror 7 semitransparent to the visible light. The field of view is thereby restricted to 30° horizontally and vertically. Two light sources 8 emitting infrared light, in this case in the form of a light emitting diode, the emitted light of which is led by a thin light fibre bundle to a small prism which finally reflects towards the eye, are arranged beside the eye 4 of the person to illuminate the eye 4 obliquely from the sides so as to achieve a good contrast between the dark pupil and the surrounding iris on the image of the eye thrown upon the first plane mirror 7. A system of lenses 9 acting as a convex lens is arranged along an optical axis extending through the rotational centre of the eye and in reflexion by the plane mirror 7 in such a way, that the pupil of the eye lies substantially in the focal plane of the system of lenses, which means that light beams emitted from one point of the pupil of the eye and reflected by the first plane mirror 7 towards the system of lenses 9 will be refracted by the system of lenses 9, so that they leave this in the form of parallel light beams. The first plane mirror 7 is preferably high-reflecting just for infrared light.

A second plane mirror 10 also semitransparent to visible light and high-reflecting to infrared radiation is arranged along the optical axis passing through the system of lenses 9. The light beams emanating from the eye 4 and refracted by the system of lenses 9 are reflected by the second plane mirror 10 towards a third semitransparent plane mirror 11, through which the main part of the light beams pass, and through a band-pass filter 12, which is arranged to filter out the main part of the light not being in the wave-length field of the beams emanating from the light sources 8—in this case about 880 nm. The parallel light beams emanating from the eye then arrive to the objective 13, in the form of a convex lens, of a video camera 14. The video camera 14 has a detector plane 15 located in the focal plane of the objective 13, on which the beams emanating from one point of the eye and made parallel by the system of lenses are refracted by the objective 13 together in one point. An image of the eye 4 is in this way created on the detector plane 15 and thanks to the light sources 8 there is a good contrast in this image between the dark pupil and the surrounding iris.

The optical unit 1 also comprises a further light source 16 emitting infrared light of the same wave-length as the light sources 8. This light source 16 consists of a light emitting diode and is located in the focal plane of the system of lenses 9 and is directed so that the light emitted therefrom firstly will be reflected by the third plane mirror and then by the second plane mirror against the system of lenses 9 along the optical axis of the optical system. This means that the light beams emitted by the light source 16 will be refracted by the optical system of lenses into parallel light beams, which are reflected by the plane mirror 7 towards the cornea of the the eye. The cornea of the eye functions in such a way that it reflects a light beam inciding thereupon as if it came from a point on the half radius of curvature of the cornea, and by the fact that such a point lies in substantially the same plane as the pupil and thereby in the focal plane in the system of lenses 9 the light beams emanating from the light source 16 and reflected by the cornea of the eye will after repeated reflexion by the first plane mirror be refracted by the system of lenses 9 to parallel beams, which are reflected by the second plane mirror 10, pass through the third plane mirror 11 and the band-pass filter 12 and finally are refracted by the objective 13 into an image of the cornea reflex on the detector plane 15 of the video camera 14. It will be explained later on that the gaze direction of the eye may be determined from the pieces of information about the position of the cornea reflex and the pupil on the detector plane 15.

A video monitor 17 is arranged in a fixed position on the carrier and with respect to the other optical elements just described. A video monitor 17 is arranged to show pictures with different symbols, which the person may hold his gaze at so as to communicate with the environment, control the video monitor or any machine or the like, to the eye 4 of the person. The video monitor 17 emits picture light passing through the second plane mirror 10 and the system of lenses 9 and is then reflected by the first plane mirror 7 towards the eye 4 of the person, so that a visible virtual picture 18 is obtained behind the plane mirror 7. The virtual picture 18 is located at a fixed distance with respect to the eye 4 of the person, but this distance may be variated by adjusting the display plane 19 of the video monitor 17. An electronic light limiter 20 is arranged behind the plane mirror 7 to regulate the extent of light from the environment 6. The electronic light limiter 20 may be controlled by the person by looking through the eye 4 at a suitable symbol on the virtual picture 18 displayed by the video monitor. The virtual picture is in reality of course located at a considerable distance in front of the optical unit, namely between 30 cm and at an indefinite sight distance therefrom.

Picture signals emanating from the detector plane of the video camera 14 are led to a picture evaluating unit 21 included in the central processing unit 3 and arranged to evaluate these picture signals and from them and other information about the parameters in the optical system previously described calculate the gaze direction of the eye 4 of the person. Then the evaluating unit 21 sends information about at which point on the virtual picture the person is looking onto a fixation unit 22, which is arranged to determine whether the gaze direction of the user corresponds to any command, i.e. whether the gaze direction lies within or without the hit region centered around each fixation point. The fixation unit 22 also decides if the eye is completely still or roving and whether the user has fixed the gaze for a time long enough to make a command considered as selected. If all conditions are met with the fixation unit 22 will send a signal to a command system 23, which in principle is a computer program package with different command procedures, which in the practice define what may be carried out with the product. Furthermore the carrying out of a command is indicated by immediate light signalization and/or by visual indication adjacent to the symbol in question on the virtual picture through a menu system 24. The command system 23 is arranged to send control signals to the menu system 24, which in its turn controls the video monitor 17 to display different menus to the eye 4 of the person. Furthermore, the command system 23 is also adapted to send control parameters to the fixation unit 22. The electronic light limiter 20 may also be controlled through the command system 23. This whole controlling may be carried out by the person in question by looking at different symbols or fields of the virtual picture 18 shown by the video monitor 17. The command system 23 also contains the routines 25, which enable two-way communication with equipments 26, which are connected to the central processing unit 3. The equipments 26 may comprise a pointing-out screen, an alarm and calling apparatus, optional accessories and the like.

Figure 7:
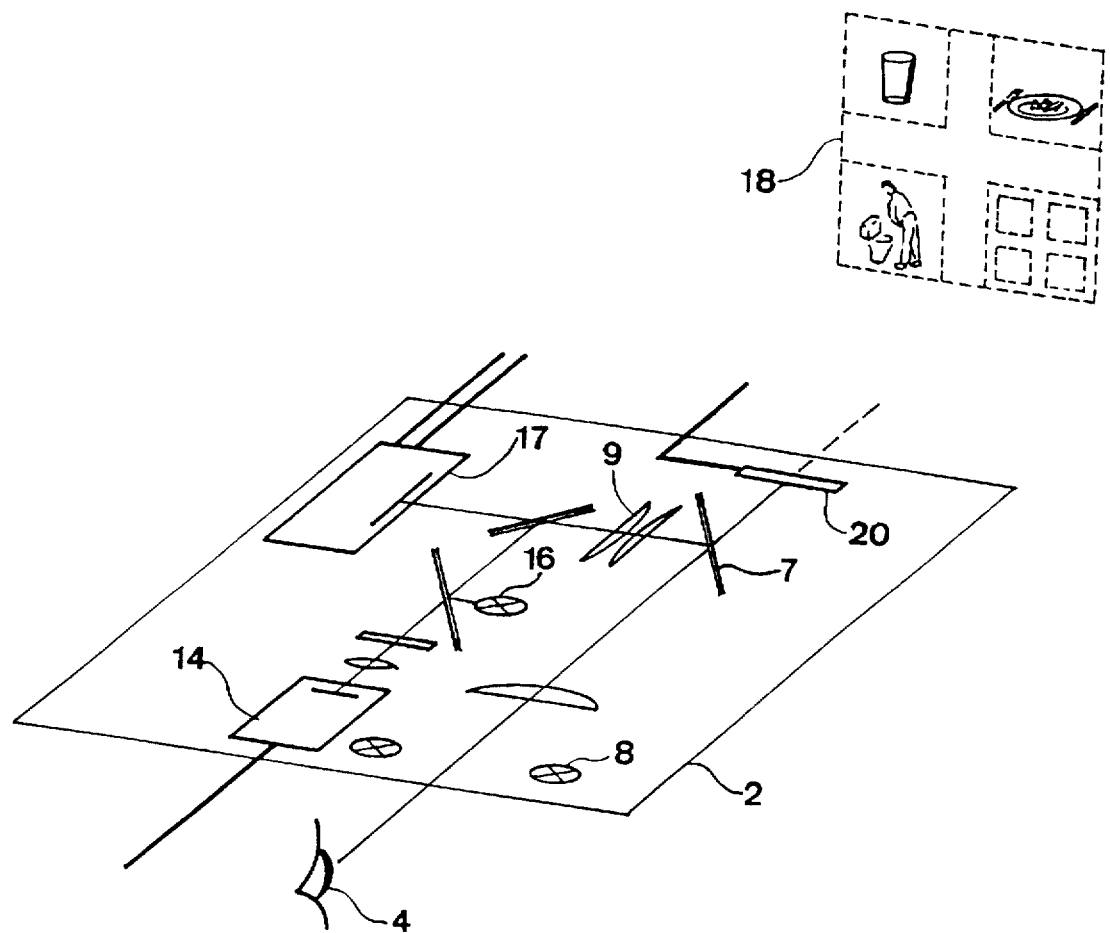
FIG. 7 is a simplified schematic perspective view of a part of the device according to the invention.

The function of the device, which can be understood by means of the abovementioned, is very diagrammatically illustrated in the appended FIG. 7.

The purpose of the device according to the invention is to determine accurately towards which point on the virtual picture 18 the gaze of the eye 4 of the person is directed also when the carrier 2, i.e. the optical unit 1, is slightly laterally displaced with respect to the eye 4 of the person. The way to obtain this and the considerations and calculations behind this will be explained below with reference to FIGS. 3–6 also.

When the user is studying a fixation point on the virtual picture the eye 4 is turned by an angle A with respect to the optical axis. In order to decide on which of the fixation points of the virtual picture the eye is fixed to, the angle of rotation A of the eye must be determined. It will now be explained how this may be achieved in an accurate manner despite a lateral displacement of the optical unit with respect to the eye.

The parallel light emanating from the light source 16 and inciding towards the eye is partially reflected by the cornea of the eye, which acts as a convex, spherical mirror with the radius of curvature r. The beam intersecting the centre of the cornea globus is reflected directly in the opposite direction, while the other beams are reflected in varying directions, and for small angles it is true that they are reflected as if they came from a point at a distance r/2 from the front edge of the cornea. Such points at the distance r/2 from the front edge of the cornea lie in substantially the same plane being perpendicular to the optical axis of the optical system and coinciding with the focal plane of the system of lenses 9.

The lateral displacement of the light reflex as a function of the distortion of the eye, i.e. the angle, is the same as the lateral displacement of the centre of the cornea sphere, i.e.

$$k = p \sin A \quad (1)$$

in which p is the distance between the rotation centre of the eye and the centre of the cornea sphere. Furthermore, it appears as when the eye is laterally displaced with respect to the optical axis the total displacement of the reflex will be $$l = b + p \sin A \quad (2)$$

A point-like light source at the distance u from the optical axis gives rise to a parallel beam bundle inciding with the angle C, given by the relation $$u/f = \tan C \quad (3)$$

in which f is the focal distance of the system of lenses.

The distance of the reflex, e, from the optical axis will then be $$e = (r/2) \tan C \quad (4)$$

after inserting (3) in (4) the enlarging factor of the image will be $$K = e/u = r/(2f) \quad (5)$$

Figure 5:
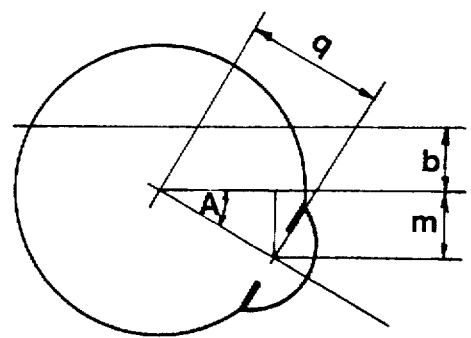

The pupil pu is located at the distance q from the rotation centre of the eye (see FIG. 5). The displacement of the pupil centre from the optical axis as a function of the distortion A of the eye will be $$m = q \sin A \quad (6)$$

If the eye is laterally displaced by the distance b with respect to the optical axis the total displacement will instead be $$n = b + q \sin A \quad (7)$$

Figure 6:
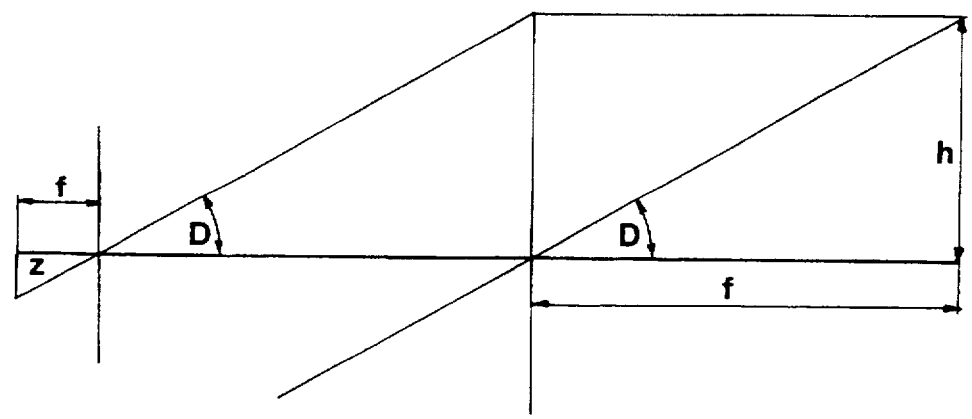

Reference is now also made to FIG. 6. The eye 4 located in the focal plane of the system of lenses 9 emits beams from a picture point at the distance h from the optical axis and creates a parallel beam bundle with the angle D out of the system of lenses given by the relationship $$h/f = \tan D \quad (8)$$

The beam bundle is refracted together by the lens of the camera objective to a point z in the detector plane 15, which is given by the relationship $$z/f_{obj} = \tan D \quad (9)$$

in which fobj is the focal distance of the objective. From this follows that the enlarging factor L of the camera image will be $$L = z/h = f_{obj}/f \quad (10)$$

The total enlarging factor M for the image of the reflex lightening will through multiplication by (5) be $$M = KL = (rf_{obj})/(2f^2) \quad (11)$$

the relation (1) and (6) give for the distortion of the reflex and pupil centre $$z(rc) = Lp \sin A \quad (12)$$

and $$z(pc) = Lq \sin A \quad (13)$$

Furthermore, the size of the pupil and reflex illumination, d and u, respectively are given by $$z(rs) = M2u \quad (14)$$

and $$z(ps) = Ld \quad (15)$$

From (2) and (7) it is noted that the difference between the distortion of the pupil and the reflex will be independent of the lateral displacement 1, so that $$z(prc) = z(ps) - z(rs) = L(q-p) \sin A \quad (16)$$

The evaluating unit 21 calculates by means of this equation the angle A and thus the distortion of the eye. L is obtained through the equation (7), Z(prc) is measured by the detector plane 15 of the video camera and q and p are constant parameters stored in the picture evaluating unit. Thus, it appears that the difference between the distortion of the pupil and the reflex will be totally independent of the lateral displacement of the optical unit with respect to the eye. The device may thanks to this fact deliver reliable results even if the optical unit is displaced somewhat with respect to the eye. The evaluating unit will still be able to reliably calculate the distortion of the eye and thus determine towards which point on the picture displayed by the video monitor the gaze of the eye is directed.

In the case in question f=80 mm, $f_{obj}$=16 mm, q=10.1 mm and p=5.3 mm. This results in L=0.20 and M=0.010, so that for the distortion A=20°:

z(rc)=0.36 mm or c. 18 micrometers/degree
z(pc)=0.69 mm or c. 35 micrometers/degree
z(rs)=0.03 mm (u=1.5 mm)
z(ps)=1.6 mm (d=8 mm)
z(prc)=0.33 mm or c. 17 micrometers/degree The detector used has the following data.

Detector surface=6.0×4.5 mm
size of the picture element=10×15.6 micrometers
vertical resolution=288 lines
horizontal resolution=600 picture points.
288 lines in 4.5 mm correspond to c. 15.6 micrometers/line.

At the distortion A=20° and the maximum pupil diameter the outer edge of the pupil lands at the distance 0.69+1.6/2 mm=1.49 mm from the centre point of the picture element. The distance to the picture border will then be 4.5/2−1.49=0.76 mm, which results in a maximally allowed decentering, i.e. lateral displacement, of the eye in the eye plane of about 0.76/0.2=3.8 mm. This has turned out to be quite sufficient.

Thus, the invention is based on the understanding that information may be obtained from an image of the eye being in a connection, which is independent of a lateral displacement of the optical unit with respect to the eye, and that these pieces of information may be used to calculate the distortion or angle of the eye, so that the result of such a calculation is independent of possible lateral displacements of said kind. In order to achieve this the particular properties of the cornea of the eye and particular arrangement of different components of the optical system with respect to each other and with respect to the eye are used, so that light emitted, or more accurately reflected, by the cornea as well as by the pupil will substantially emanate from the focal plane of the system of lenses.

The invention is of course not limited to the preferred embodiment described above, but several modification possibilities thereof would be apparent to a person skilled in the art without diverting from the spirit of the invention.

It would for example be conceivable to choose any other point following the eye in its motion than the pupil. A contact lens provided with a mark may for instance be placed on the eye of the person and the position of this mark in the detector plane could be used instead of the position of the pupil.

Furthermore, it would of course be possible to change the components of the optical system for other components having a similar function. The arrangement of these components on the carrier may also be other than in the case shown, so that the beam path will be another.

We claim:

1. A device for enabling a person without capability to speak and move their arms to communicate with the environment, comprising:

a frame;

a light sensitive element mounted on said frame;

illumination means for illuminating an eye of the person;

a parallel beam source mounted on said frame for generating parallel light beams and directing said beams to said eye so that said beams reflect from a cornea of the eye to generate a cornea reflex;

means on said frame for focusing an image of said eye and an image of said cornea reflex on said light sensitive element, said image of said eye including an image of a pupil of said eye;

detecting means operatively connected to said light sensitive element for detecting a relative position of said image of said pupil and said image of said cornea reflex on said light sensitive element;

a picture apparatus mounted on said frame for displaying at least one picture to the person so that the person can gaze at a selected one of said pictures;

evaluating means operatively connected to said detecting means for calculating from said relative position a gaze direction of said eye, to determine to which point on said picture said gaze is directed;

a first semitransparent plane mirror mounted on said frame so that light from said picture apparatus passes through said first mirror and is visible to said eye and so that said images of said pupil and said cornea reflex are reflected by said first mirror onto said light sensitive element;

a second semitransparent plane mirror on said frame interposed between said first plane mirror and said light sensitive element; and said parallel beam source including a light source, said second plane mirror being positioned so that light from said light source reflects from said second plane mirror to said first plane mirror and from said first plane mirror along a path of light to said eye, said parallel beam source including convex lens means on said frame positioned along said path of light between said first plane mirror and said eye, said convex lens means having a focal length, said convex lens means being positioned so that light from said light source travels a distance of said focal length from said light source to said convex lens means on a first side of said convex lens means, so that light from said light source forms parallel light beams on a second side of said convex lens means opposite said first side.

2. The device defined in claim 1 wherein said parallel light beams define an optic axis, said image of said pupil has a center, and said gaze direction forms an angle with said optic axis, the sine of said angle being proportional to the distance between said center and said cornea reflex image.

3. The device of claim 2 wherein the frame is a carrier fixable relative to a person's head.

4. The device according to claim 3 wherein the carrier is positioned on the person's head such that the center of a cornea sphere of the eye of the person is at a distance which is substantially half the radius of curvature of the cornea behind a focal plane of the convex lens on said second side, so that the parallel light beams from the light source are refracted and become parallel to each other when emerging on the first side.

5. The device according to claim 4, wherein the light sensitive element is a camera, an objective of the camera located on said first side with its optical center on the optical axis so that the parallel light beams emanating from the cornea reflex are refracted together to a point in the focal plane of the camera objective.

6. The device according to claim 2, wherein the picture apparatus is arranged along the optical axis, and the picture apparatus showing a picture by emitting the picture along the optical axis.

7. The device of claim 1 wherein the picture has a plurality of symbols or text corresponding to different items of information, the point on said picture to which said gaze is directed being a selected one of the symbols or text.

8. The device of claim 1 wherein the evaluation means include means for selecting at least two pieces of image information, from the image of the eye on the light sensitive element, the two pieces of image information being selected as a function of an angle of a gaze direction of the eye and an optical axis defined by the parallel light beams, substantially independent of small lateral displacements.

9. The device of claim 8 wherein one piece of image information is a light reflex emanating from the cornea of the eye and the other piece of image information is an image of a pupil opening of the eye.

10. The device according to claim 1, further comprising a third plane mirror located between the second plane mirror and the light sensitive element, the third plane mirror being semi-transparent for letting light beams reflected by the second plane mirror towards the light sensitive element through, said third plane mirror arranged to reflect light emitted by said light source towards the second plane mirror so that it is reflected towards the convex lens means.

* * * * *